(12) United States Patent
Yang

(10) Patent No.: US 10,540,997 B2
(45) Date of Patent: *Jan. 21, 2020

(54) LUBRICANT COMPOSITIONS

(71) Applicant: Seagate Technology LLC, Cupertino, CA (US)

(72) Inventor: Jiping Yang, San Jose, CA (US)

(73) Assignee: SEAGATE TECHNOLOGY LLC, Cupertino, CA (US)

(*) Notice: Subject to any disclaimer, the term of this patent is extended or adjusted under 35 U.S.C. 154(b) by 219 days.

This patent is subject to a terminal disclaimer.

(21) Appl. No.: 15/693,372

(22) Filed: Aug. 31, 2017

(65) Prior Publication Data

US 2017/0365287 A1    Dec. 21, 2017

Related U.S. Application Data

(63) Continuation of application No. 14/788,654, filed on Jun. 30, 2015, now Pat. No. 9,805,755.

(Continued)

(51) Int. Cl.
*G11B 5/66* (2006.01)
*G11B 5/725* (2006.01)
(Continued)

(52) U.S. Cl.
CPC ............ *G11B 5/725* (2013.01); *C07C 43/137* (2013.01); *C10M 105/54* (2013.01)

(58) Field of Classification Search
CPC ............ C10M 107/38; C10M 2213/00; C10M 2213/04; C10M 2213/043; C10M 2213/06;

(Continued)

(56) References Cited

U.S. PATENT DOCUMENTS 6,608,009 B2 * 8/2003 Akada ................ C07F 9/65815
508/422
7,683,012 B2 * 3/2010 Burns ................ C10M 107/38
428/810

(Continued)

OTHER PUBLICATIONS

Marchon et al., "Fomblin Multidentate Lubricants for Ultra-Low Magnetic Spacing," IEEE Trans Magn, vol. 42, No. 10, Oct. 2006, pp. 2504-2506.*

*Primary Examiner* — Holly C Rickman
(74) *Attorney, Agent, or Firm* — Holtzer Patel Drennan

(57) ABSTRACT

Provided herein is a lubricant including a compound of Formula I $$L-(CF_2CF_2O)_n-CF_2CH_2O-N-OCH_2CF_2O-(CF_2CF_2O)_m-M \quad \text{(Formula I)}$$

wherein
L is selected from the group consisting of

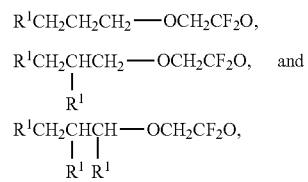

M is selected from the group consisting of (Continued)

-continued

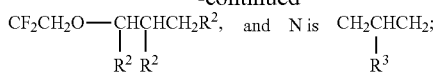

wherein each instance of $R^1$, $R^2$, and $R^3$ is independently selected from the group consisting of hydroxyl, alkoxyl, carbocycyl, phenyl, heterocycyl, piperonyl, carboxyl, alkylamido, acetamido, carbamoyl, N-alkylcarbamoyl, N,N-dialkylcarbamoyl, 2,3-dihydroxy-1-propoxyl, acryloyl, alkacryloyl, methacryloyl, a sustituent of methyl methacrylate, and a substituent of glycidyl ether; and
wherein
$n \geq 1$,
$m \geq 1$, and
n and m are the same or different.

20 Claims, 6 Drawing Sheets

Related U.S. Application Data

(60) Provisional application No. 62/109,030, filed on Jan. 28, 2015.

(51) Int. Cl.
*C07C 43/13* (2006.01)
*C10M 105/54* (2006.01)

(58) Field of Classification Search
CPC ......... C10M 2213/0606; C10M 105/54; G11B 5/725; C10N 2040/18; C10N 2240/204; C08G 65/007; C08G 2650/48; C09D 171/00; C09D 171/02; Y10T 428/1164; C07C 43/137
See application file for complete search history.

(56) References Cited

U.S. PATENT DOCUMENTS

| | | | |
|---|---|---|---|
| 8,586,703 B2* | 11/2013 | Yang | C08G 65/007 427/127 |
| 9,805,755 B1* | 10/2017 | Yang | C07C 43/137 |
| 2002/0119316 A1* | 8/2002 | Shukla | C23C 14/0605 428/408 |
| 2014/0029137 A1* | 1/2014 | Musashi | G11B 5/725 360/99.08 |

* cited by examiner

LUBRICANT COMPOSITIONS

CROSS-REFERENCE

This application claims the benefit of U.S. Provisional Patent Application No. 62/109,030, filed Jan. 28, 2015. This application is a continuation of prior U.S. patent application Ser. No. 14/788,654, filed Jun. 30, 2015.

BACKGROUND

High-performance lubricants are used in a large number of diverse applications. The requirements of these lubricants are becoming more demanding due to a variety of factors, including increased miniaturization of electronic and mechanical devices, higher-temperature operating conditions, increased expectations for product lifetimes, and expanded ranges of operating and storage environments.

One application in which high-performance lubricants are subject to ever-increasing demands is in magnetic recording apparatuses such as hard disk drives. Some lubricants for hard disk drives include perfluoropolyethers. There remains, however, a need for optimizing PFPE lubricants to meet such ever-increasing demands.

SUMMARY

Provided herein is a lubricant including a compound of Formula I $$L\text{-}(CF_2CF_2O)_n\text{---}CF_2CH_2O\text{---}N\text{---}OCH_2CF_2O\text{---}(CF_2CF_2O)_n\text{-}M \quad \text{(Formula I)}$$

wherein
L is selected from the group consisting of

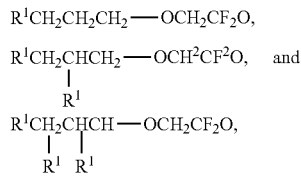

M is selected from the group consisting of

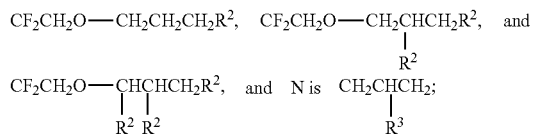

wherein each instance of $R^1$, $R^2$, and $R^3$ is independently selected from the group consisting of hydroxyl, alkoxyl, carbocycyl, phenyl, heterocycyl, piperonyl, carboxyl, alkylamido, acetamido, carbamoyl, N-alkylcarbamoyl, N,N-dialkylcarbamoyl, 2,3-dihydroxy-1-propoxyl, acryloyl, alkacryloyl, methacryloyl, a substituent of methyl methacrylate, and a substituent of glycidyl ether; and wherein
$n \geq 1$,
$m \geq 1$, and
n and m are the same or different.

Also provided herein is a lubricant including a compound of Formula II $$(OH)CH_2CH(OH)CH_2\text{---}OCH_2CF_2O\text{---}(CF_2CF_2O)_n\text{---}CF_2CH_2O\text{---}CH_2CH(OH)\text{---}CH_2\text{---}OCH_2CF_2O\text{---}(CF_2CF_2O)_m\text{---}CF_2CH_2O\text{---}CH_2CH(OH)CH_2(OH) \quad \text{(Formula II)}$$

wherein
$n \geq 1$,
$m \geq 1$, and
n and m are the same or different.

Also provided herein is an apparatus including a substrate; a magnetic layer over the substrate for magnetic recording; a protective overcoat for protecting the magnetic layer; and a layer of lubricant over the protective overcoat. The lubricant may include one or more compounds selected from Formulas I and II.

DRAWINGS

FIG. 1 provides a block diagram of an apparatus for magnetic recording including a lubricant layer in accordance with some embodiments.

FIGS. 2A and 2B provide diagrams comparing flying head distance from the flying head to (A) a surface with a conventional lubricant layer and (B) a surface with a lubricant layer including a compound selected from Formulas I and II in accordance with some embodiments.

FIG. 3 provides example compounds of Formulas I and II, any of which may be used as a lubricant or in a lubricant in accordance with some embodiments.

FIG. 4 provides an example of a preparation for the compounds of FIG. 3 in accordance with some embodiments.

DESCRIPTION

Figure 1:
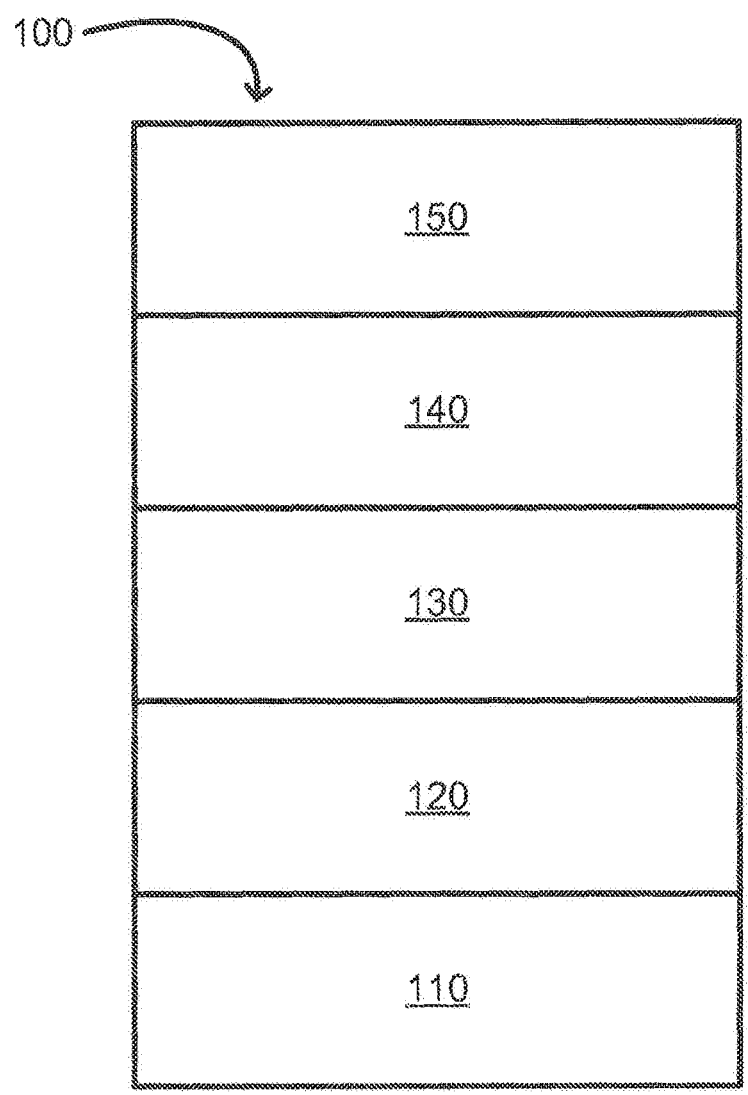

Before some particular embodiments are provided in greater detail, it should be understood by those of ordinary skill in the art that the particular embodiments do not limit the scope of the concepts provided herein, as features of such particular embodiments may vary. It should likewise be understood that a particular embodiment has features that may be readily separated from the particular embodiment and optionally combined with or substituted for features of any of a number of other embodiments provided herein.

It should also be understood by those of ordinary skill in the art that the terminology used herein is for the purpose of providing some particular embodiments, and the terminology does not limit the scope of the concepts provided herein. Unless indicated otherwise, ordinal numbers (e.g., first, second, third, etc.) are used to distinguish or identify different features or steps in a group of features or steps, and the ordinal numbers do not supply a serial or numerical limitation. For example, "first," "second," and "third" features or steps need not necessarily appear in that order, and the particular embodiments need not necessarily be limited to the three features or steps. Unless indicated otherwise, any labels such as "left," "right," "front," "back," "top,"

"bottom," "forward," "reverse," "clockwise," "counter-clockwise," "up," "down," or other similar terms such as "upper," "lower," "aft," "fore," "verticle," horizontal," "proximal," "distal," and the like are used for convenience and are not intended to imply, for example, any particular fixed location, orientation, or direction. Instead, such labels are used to reflect, for example, relative location, orientation, or direction. Unless indicated otherwise, singular forms of "a," "an," and "the" include plural forms unless the context clearly dictates otherwise.

Unless defined otherwise, all scientific and technical terms used herein have the same meaning as commonly understood by those of ordinary skill in the art.

1. Definitions

As used in this application, the following words or phrases include the meanings specified.

A "storage medium" (plural: "storage media") or "recording medium" (plural: "recording media") includes any apparatus that can store information such as digital data. The storage medium may be in the form of a thin magnetic film, for example, a magnetic film of cobalt, platinum, and/or chromium alloy over a supporting substrate. One example of a supporting substrate is a nickel-phosphorous-plated aluminum or glass disk. The storage medium may also have a protective layer or overcoat applied over the magnetic film. An example of a protective overcoat includes, but is not limited to, amorphous carbon such as diamond-like carbon.

A "recording layer" or "recording surface" includes a portion of a storage medium adapted for magnetic recording of information. The magnetic recording may be effected by a magnetic head (or read-write head) assembly flying over the recording layer or recording surface. The magnetic head assembly may be mounted on a slider with an air-bearing surface for flying over the recording surface.

A "data zone" includes a zone over which the magnetic head assembly flies, in which the magnetic head assembly magnetically writes information, and from which the magnetic head assembly magnetically reads information. The data zone may have a roughness average of less than about 15 Å, or a roughness average of less than about 10 Å.

A "fluoropolyether" ("FPE") includes a compound or polymer composed of at least some fluoroalkyloxy units (e.g., $CH_2CF_2O$—, —$CF_2CH_2O$—, —$CH_2CH_2CF_2O$—, —$CH_2CF_2CF_2O$—, —$CH_2CF_2CH_2O$—, $CF_2CF_2CH_2O$—, —$CF_2CH_2CH_2O$—, —$CF_2CH_2CF_2O$— etc.) some of which may optionally be perfluoroalkyloxy units (e.g., —$CF_2CF_2O$—, $CF_2CF_2CF_2O$—, etc.). A "per£luoropolyether" ("PFPE") includes a compound or polymer composed of perfluoroalkyloxy units. Examples of commercially available FPEs and PFPEs include, but are not limited to, Fomblin Z (random copolymer of $CF_2CF_2O$ and $CF_2O$ units), Fomblin Y (random copolymer of $CF(CF_3)$ $CF_2O$ and $CF_2O$), and functional derivatives of Fomblin Z or Fomblin Y such as ZDOL, ZDOL TX, and Z-TETRAOL, available from Montedison S. p. A (Milan, Italy); Demnum™ available from Daikin America, Inc. (Orangeburg, N.Y.); and DuPont™ Krytox®.

"Backbone" includes a main chain of a compound or polymer such as the main chain of an FPE or a PFPE. Elements of the backbone may includecarbon (C), nitrogen (N), oxygen (O), or other linker elements. The backbone of an FPE or a PFPE, itself, does not bond to a surface (e.g, diamond-like carbon surface) over which the FPE or the PFPE is applied. However, the backbone of the FPEs provided herein may interact with or bond to such a surface through intervening non-terminal functional groups.

A "functional group" includes a functionalized substituent attached to a chain (e.g., main chain or backbone; side chain; etc.) of an FPE that is capable of interacting or bonding with a surface over which the FPE is applied. Examples of functional groups that may be used include, but are not limited to, any one or more of hydroxyl, alkoxyl, carbocycyl, phenyl, heterocycyl, piperonyl, carboxyl, alkylamido, acetamido, carbamoyl, N-alkylcarbamoyl, N,N-dialkylcarbamoyl, 2,3-dihydroxy-1-propoxyl, acryloyl, alkacryloyl, methacryloyl, a substituent of methyl methacrylate, and a substituent of glycidyl ether. Functional groups may cause the FPEs to interact with or bond to a surface through one or more intermolecular interactions (e.g., polar interactions) adhering the FPEs to a surface. If methacryloyl, a substituent of methyl methacrylate, or a substituent of glycidyl ether is used, then ultraviolet light may optionally be used to activate the bonding enhancer.

A "terminal functional group" includes a functional group that is attached to a linker element of the backbone or a side chain thereof on an end of the backbone or the side chain thereof.

A "non-terminal functional group" includes a functional group that is attached to a linker element of the backbone or a side chain thereof that is not at an end of the backbone or the side chain thereof. A non-terminal functional group may be attached at any one or more points along the backbone or the side chain thereof. One or more non-terminal functional groups may be provided in order to reduce the height that the backbone extends from the surface.

Various aspects of lubricants including FPEs for storage media and storage media incorporating the lubricants are provided herein below. However, as those of ordinary skill in the art will readily appreciate, the FPEs may be used in other capacities including other compositions and apparatuses.

2. Compositions

Lubricants may include one or more FPEs including a backbone, wherein each end of the backbone may terminate with one or more terminal functional groups (e.g., —OH). The one or more terminal functional groups may cause each end of the backbone to bond to a surface (e.g., diamond-like carbon-coated surface) over which the FPE is applied. One or more non-terminal functional groups (e.g., —OH) may also be attached at any point along the backbone including at or near a center of the backbone. The one or more non-terminal functional groups may cause internal points of the backbone to bond to the surface over which the FPE is applied, thereby drawing and conforming the FPE to the surface. In addition to optimizing bonding of FPEs to surfaces such as those with a carbon (e.g., diamond-like carbon) overcoat, the use of the functional groups in the foregoing configuration beneficially reduces the height that lubricants including the FPEs reach, for example, into head-media spacing ("HMS") in hard disk drives.

Lubricants may include, wholly or in part, one or more compounds of Formula I

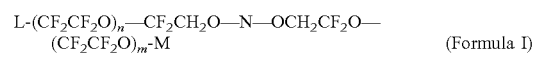   (Formula I)

wherein

L is selected from the group consisting of

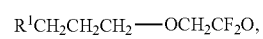

-continued

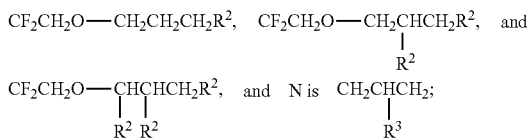

M is selected from the group consisting of

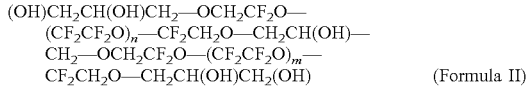

wherein each instance of $R^1$, $R^2$, and $R^3$ is independently selected from the group consisting of hydroxyl, alkoxyl, carbocycyl, phenyl, heterocycyl, piperonyl, carboxyl, alkylamido, acetamido, carbamoyl, N-alkylcarbamoyl, N,N-dialkylcarbamoyl, 2,3-dihydroxy-1-propoxyl, acryloyl, alkacryloyl, methacryloyl, a substituent of methyl methacrylate, and a substituent of glycidyl ether; and
wherein
$n \geq 1$,
$m \geq 1$, and
n and m are the same or different.

Lubricants may include, wholly or in part, one or more compounds of Formula II $$(OH)CH_2CH(OH)CH_2\text{—}OCH_2CF_2O\text{—}$$
$$(CF_2CF_2O)_n\text{—}CF_2CH_2O\text{—}CH_2CH(OH)\text{—}$$
$$CH_2\text{—}OCH_2CF_2O\text{—}(CF_2CF_2O)_m\text{—}$$
$$CF_2CH_2O\text{—}CH_2CH(OH)CH_2(OH) \quad \text{(Formula II)}$$

wherein
$n \geq 1$,
$m \geq 1$, and
n and m are the same or different.

For lubricants including one or more compounds selected from Formulas I and II, the values of n and m, each of which may be greater than or equal to 1 (e.g., $\geq 1$, 2, 3, 4, 5, etc.), may be selected so as to provide compounds having a molecular weight that falls within a desired average range. The average molecular weight range, for example, may range from about 1000 dalton ("Da") to about 7000 Da, including from about 1000 Da to about 5000 Da, such as about 2000 Da to about 4000 Da.

Compared to other lubricants, lubricants including one or more compounds selected from Formulas I and II provide higher resistance to head-media contact (e.g., higher power is needed during a shock event to put the head into contact with underlying media); lower lubricant pickup by head (e.g., the low-flying or media-contacting head picks up less lubricant); lower negative burnish; and lower HMS, which, in turn, leads to higher areal density.

Figure 2A:
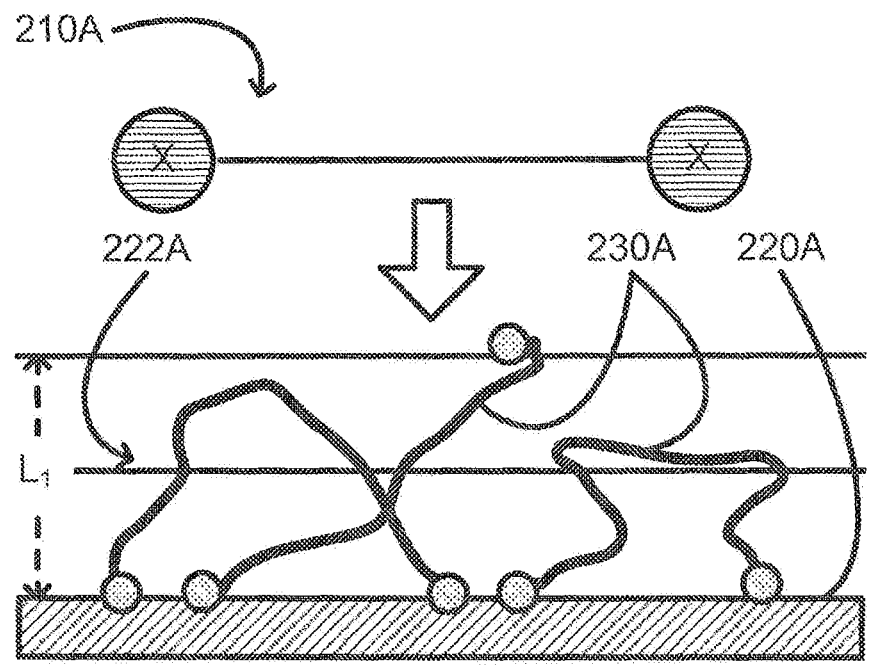
Figure 2B:
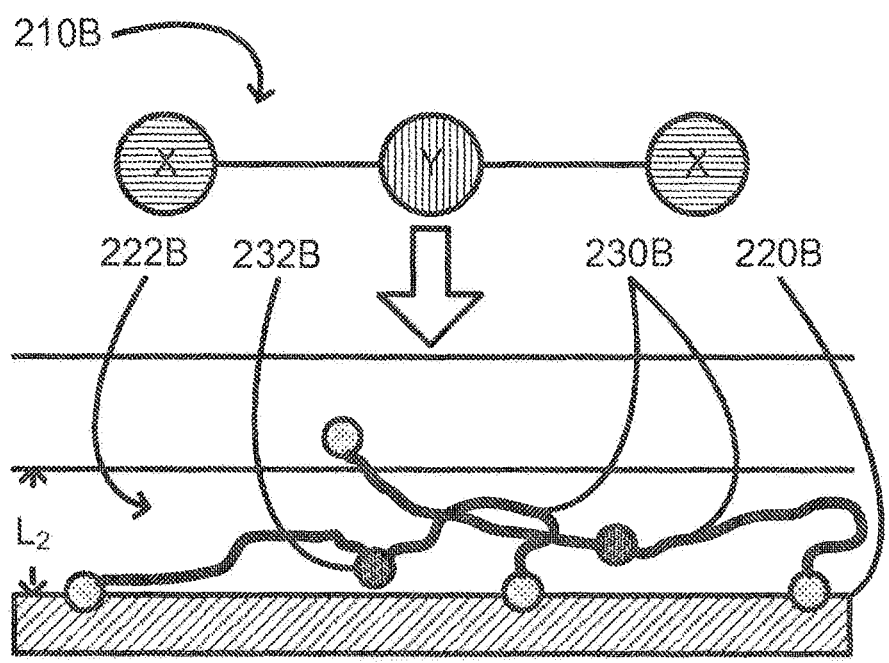

With respect to lower HMS, FIGS. 2A and 2B illustrate the difference in distance between a flying head 210A (210B) and 1) a lubricated surface 220A when using a conventional lubricant 230A in a lubricant layer 222A (FIG. 2A) and 2) a lubricated surface 220B when using a lubricant including a compound of Formula I or Formula II 230B in the lubricant layer 222B (FIG. 2B). The height L1 that the conventional lubricant 230A extends from the lubricated surface 220A is significantly greater than the height L2 that the lubricant including the compound of Formula I or Formula II 230B extends from the lubricated surface 220B.

The conventional lubricant may include an FPE or a PFPE lacking non-terminal functional groups attached to a backbone thereof. Lubricants including one or more compounds selected from Formulas I and II 230B may include one or more non-terminal functional groups 232B attached at any one or more points along the backbone or a side chain thereof. One or more non-terminal functional groups may reduce the height the compounds selected from Formulas I and II extend from the surface (e.g., lubricated surface 220B) Consequently, the distance between the flying head 210B and the surface may be significantly smaller for the lubricant including a compound of Formula I or Formula II than the distance between the flying head 210A and surface when a conventional lubricant is used.

3. Apparatuses Incorporating the Lubricant, and Methods for Lubricating

Apparatuses such as storage media including a lubricant layer formed from lubricants including one or more compounds selected from Formula I and II are provided. Methods for lubricating apparatuses such as storage media may include lubricating, either wholly or in part, with one or more compounds selected from Formulas I and II as provided With respect to the apparatuses, FIG. 1 provides an illustration showing the layers of a storage medium including a substrate 110, a seed layer 120, a magnetic layer 130, a protective layer 140, and a lubricant layer 150. The initial layer of the media structure is the substrate 110, which may be a nickel-phosphorous-plated aluminum or glass disk. The seed layer 120 may be a thin film deposited onto the substrate 110, which thin film may be chromium. The magnetic layer 130 may be a thin film deposited on top of the seed layer 120, which thin film may be a magnetic alloy including cobalt (Co), platinum (Pt), and/or chromium (Cr) alloy. The magnetic layer may be applied at a thickness of about 500 Å over the substrate.

The protective layer 140 is a thin film deposited on top of the magnetic layer 130. The protective layer 140 may be a diamond-like carbon ("DLC") layer, which exhibits properties between those of graphite and diamond. The DLC layer may be deposited using thin film deposition techniques such as one or more thin film deposition techniques selected from ion beam deposition (IBD), plasma enhanced chemical vapor deposition (PECVD), magnetron sputtering, radio frequency sputtering, and chemical vapor deposition (CVD) During the deposition process, adjusting sputtering gas mixtures of argon and hydrogen varies the concentrations of hydrogen found in the DLC. The protective layer may be about 150 Å thick, or the protective layer may be less than 150 Å thick, such as less than 100 Å thick.

Lubricant layer 150 including one or more compounds selected from Formulas I and II may be deposited on top of the protective layer 140 for added protection, lubrication, and enhanced disk drive reliability. Lubricant layer 150 reduces wear and damage caused by occasional contacts of the magnetic head assembly with the storage medium.

The durability and reliability of storage media is achieved primarily by the application of the protective layer 140 and the lubricant layer 150. As the thickness of the protective layer 140 and the lubricant layer 150 is reduced, greater integration at the interface of the protective layer 140 and the lubricant layer 150 is specified to provide a more durable protective film. The conformation of the lubricant molecules on the protective layer 140, as described in reference to the lubricated surface 220B of FIGS. 2A and 2B, is also of importance to the HMS. In addition, lubricants including one or more compounds selected from Formulas I and II with multi-point attachments to the protective layer 140 are better able to cover the entire surface of the protective layer 140 than compounds with only end-point attachments.

With respect to the methods, the methods for lubricating apparatuses such as storage media may include applying a lubricant layer over a surface to be lubricated. The lubricant layer may be formed using a lubricant including one or more compounds selected from Formulas I and II, which one or more compounds may form the lubricant either wholly or in part.

The lubricant layer such as lubricant layer 150 may be applied evenly in a thin film having a thickness from about 5 Å to about 50 Å, including from about 8 Å to about 40 Å, for example, from about 10 Å to about 20 Å. The lubricant layer may be made as thin as possible while maintaining its characteristics related to storage media durability and slider flyability. The selection of the thickness of the lubricant layer may depend on interactions between the storage medium and the magnetic head assembly, which interactions include the static friction or "sticktion" force on the slider, air shear, and/or the tendency of the lubricant to evaporate.

The methods of preparing storage media using the lubricants described herein may be incorporated into methods for manufacturing disks and disk drives. Inaccordance with these methods, more durable, higher-density storage media may be provided.

These and other aspects related to the lubricants provided herein are further described in the non-limiting Examples set forth below.

EXAMPLES

Example 1

Preparation of Compounds of Formulas I and II

Figure 3:
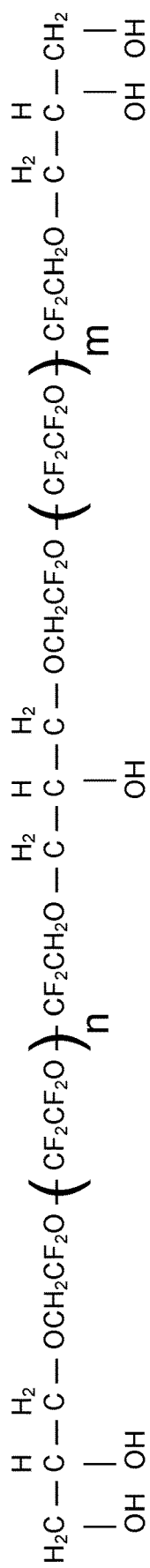
Figure 4:
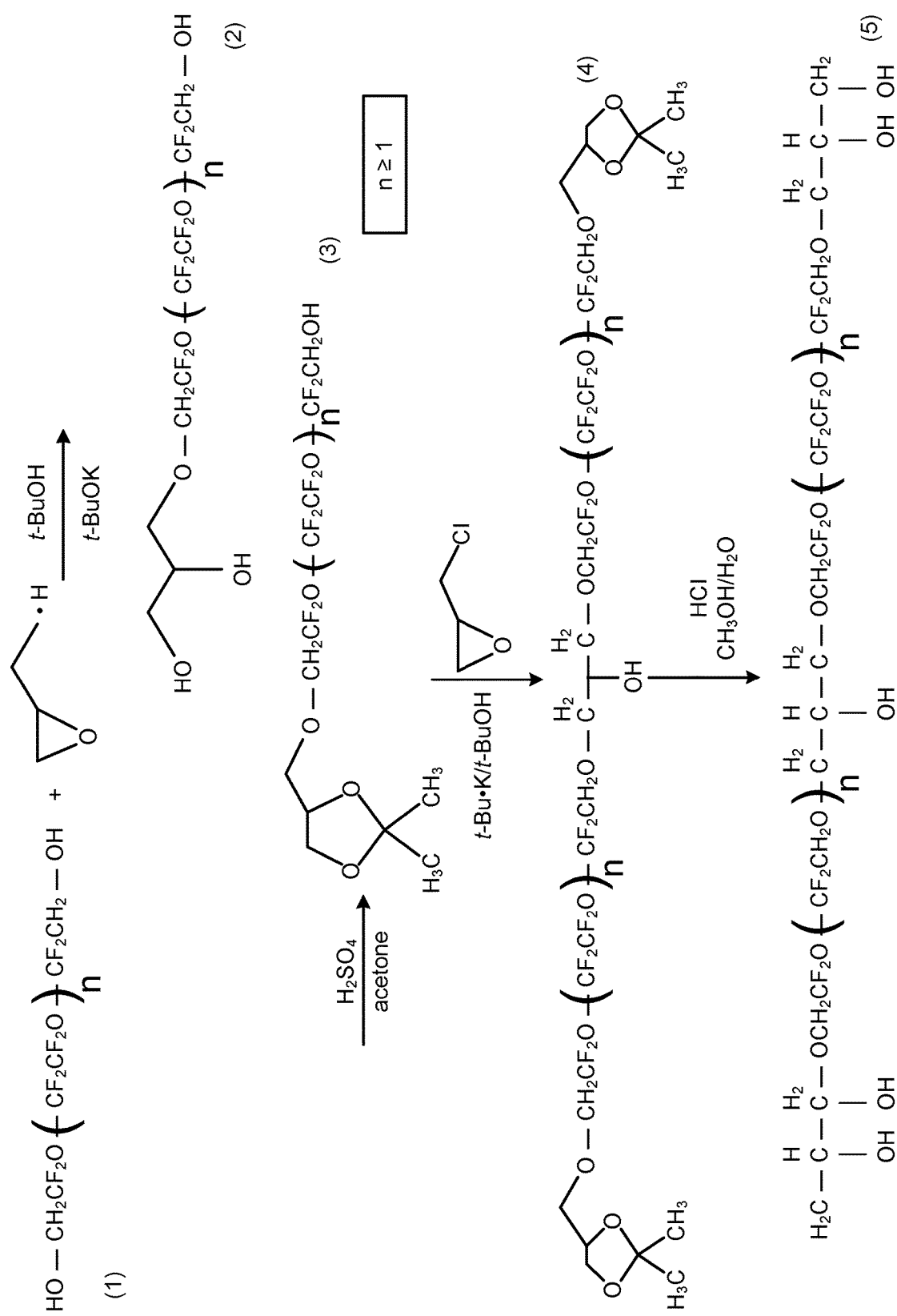

Compounds of Formulas I and II such as the compounds of FIG. 3 may be prepared by methods provided herein including the method shown in FIG. 4. Those of ordinary skill in the art will appreciate the method shown in FIG. 4 may be used to prepare a number of different compounds of Formulas I and II other than those shown in FIGS. 3 and 4. The number of different compounds of Formulas I and II may be prepared by substitution of one or more starting materials, reagents, and/or conditions with alternatives to those shown in FIG. 4 or provided in reference thereto, which may require some additional steps available to those of skill in the art. Those of ordinary skill in the art will also appreciate the compounds of Formulas I and II may also be prepared by different methods including different starting materials, reagents, and/or conditions, which methods are available to those of ordinary skill in the art.

Starting materials may be available from commercial sources such as Sigma-Aldrich Co. (St. Louis, Mo.). Starting materials may also be prepared using methods available to those of ordinary skill in the art. For example, some starting materials may be prepared using methods available in the following reference: Ho, T.-L. Fieser and Fieser's Reagents for Organic Synthesis, Vol. 27; John Wiley & Sons: New York, 2013.

Organic transformations such as functional group transformations may be used to prepare compounds of Formulas I and II. Forexample, some organic transformations may be used in accordance with organic transformations available in the following reference: Larock, R. C. Comprehensive Organic Transformations, A Guide to Functional Group Preparations, $2^{nd}$ ed.; John Wiley & Sons: New York, 1999.

Protecting group methodologies for protecting/de-protecting functional groups may be used to prepare compounds of Formulas I and II. For example, some protecting group methodologies may be used in accordance with protecting group methodologies available in the following reference: Greene, T. W.; Wuts, P. G. M. Protective Groups in Organic Synthesis, $3^{nd}$ ed.; John Wiley & Sons: New York, 1999.

Example 1.1

Preparation of Compound (2)

To a 250 mL flask was added 152.35 g of compound (1), 50 mL of t-BuOH, and 1.58 g of potassium tert-butoxide at 65° C. Glycidol (12.17 g) was added to the mixture over 3 hours, and the reaction was carried out for 24 hours.

The reaction mixture was subsequently washed with a mixture of 75 mL of deionized ("DI") water, 50 mL of isopropyl alcohol, and 1.5 mL of 1:1 HCl. The mixture was then washed with 75 mL of DI water twice. The reaction product was recovered by rotary evaporation.

The crude product was purified by column chromatography on silica gel to afford 47 g of compound (2).

Example 1.2

Preparation of Compound (3)

To a 250 mL flask equipped with a Dean-Stark trap and condenser was added 30.60 g of Compound (2), 40 mL of acetone, 30 mL of petroleum ether, and 2 drops of 96% H2SO4. The mixture was stirred under reflux for 20 hours.

The reaction mixture was cooled down to room temperature, and 0.73 g of sodium bicarbonate was added. After stirring for 1 hour, the mixture was filtered through a 1-μm filter. Petroleum ether and acetone were removed by rotary evaporation to afford 25.46 g of compound (3) as an oily liquid.

Example 1.3

Preparation of Compound (4)

To a 250 mL flask was added 25.46 g of compound (3), 15 ml of t-BuOH, and 2.23 g of potassium tert-butoxide. The flask was immersed in a 60° C. oil bath. To the flask was added 0.92 g of epichlorohydrin over 1.5 hours, and the reaction mixture was stirred for 24 hrs.

The reaction mixture was cooled down to room temperature. The reaction mixture was subsequently washed with a mixture of 100 mL of water, 50 mL of isopropyl alcohol, and 1 ml of 1:1 HCl. The mixture was then washed with a mixture of 100 mL of water and 30 mL of isopropyl alcohol. After drying, 24.00 g of compound (4) was obtained.

Example 1.4

Preparation of Compound (5)

To a 250 mL flask was added 22.5 g of compound (4), 6.5 g of methanol, 3.5 g of water, and 0.37 g of 1:1 HCl. The reaction mixture was stirred in a 65° C. oil bath for 4 hours, and then the reaction mixture was stirred at room temperature for 1 day.

To the reaction mixture was added 10 mL DI water and 0.37 g of sodium bicarbonate. After stirring for 1 hour, the oil phase was washed with 30 mL of DI water. The oil phase was then dissolved in DuPont™ Vertrel®. The Vertrel® solution was dried over anhydrous magnesium sulfate. After removing the magnesium sulfate and solvent, 20.49 g of crude product was obtained.

The above obtained crude product was purified by column chromatography on silica gel to afford 10.1 g of compound (5).

Example 2

Clearance Capability of Lubricated Storage Media

Figure 5:
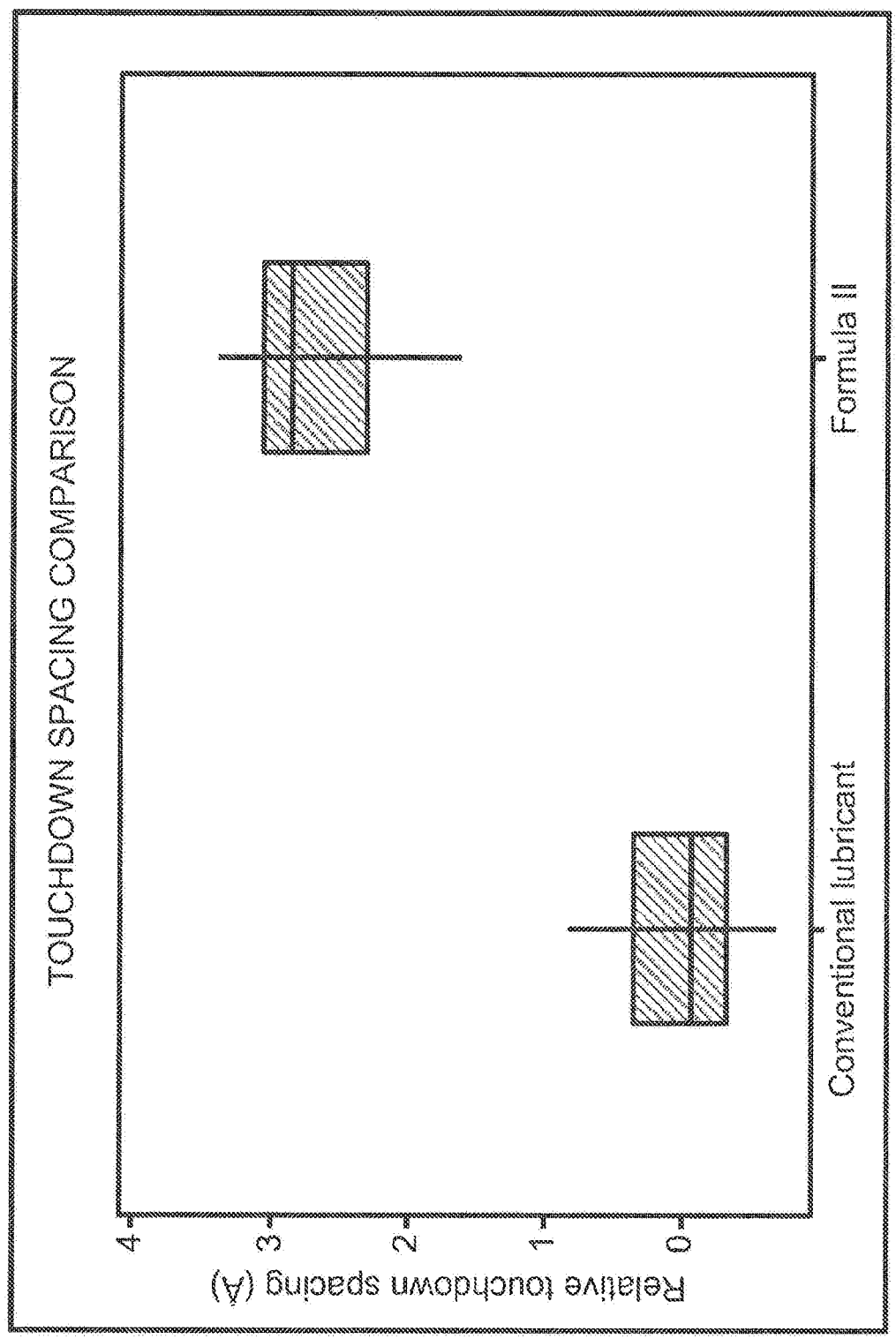
FIG. 5 is a box plot comparing relative touchdown spacing for a flying head above a surface with a conventional lubricant layer and a surface with a lubricant layer including a compound selected from Formulas I and II in accordance with some embodiments.

FIG. 5 is a box plot comparing relative touchdown spacing for a flying head above (A) a surface with a lubricant layer consisting of a conventional lubricant (e.g., Z-Tetraol) and (B) a surface with a lubricant layer including a compound selected from Formulas I and II (e.g., compound of FIG. 3). Touchdown spacing may be described as the distance between the lowest point of the flying head and the top of the lubricant surface. The touchdown spacing of a storage medium using a lubricant including a compound such as that of Formula I and/or II may result in more distance between the head and lubricant surface for a given HMS, reducing head-disc interactions and promoting disk drive reliability. Touchdown spacing such as that in FIG. 5 may be measured using an adaptive fly height head to protrude the close point of the head (keeping the flying height constant) until it touches the top of the lubricant layer, with contact determined by an increase in the acoustical emission signal from a sensor on the head. The same head may be used to measure different lubricants, which keeps the flying height constant and allows measurement of the difference in clearance between the lubricants. The conventional lubricant may be arbitrarily set to zero to show the measured difference in clearance from the lubricant.

Example 3

TOC Pick-Up of Lubricants

Figure 6:
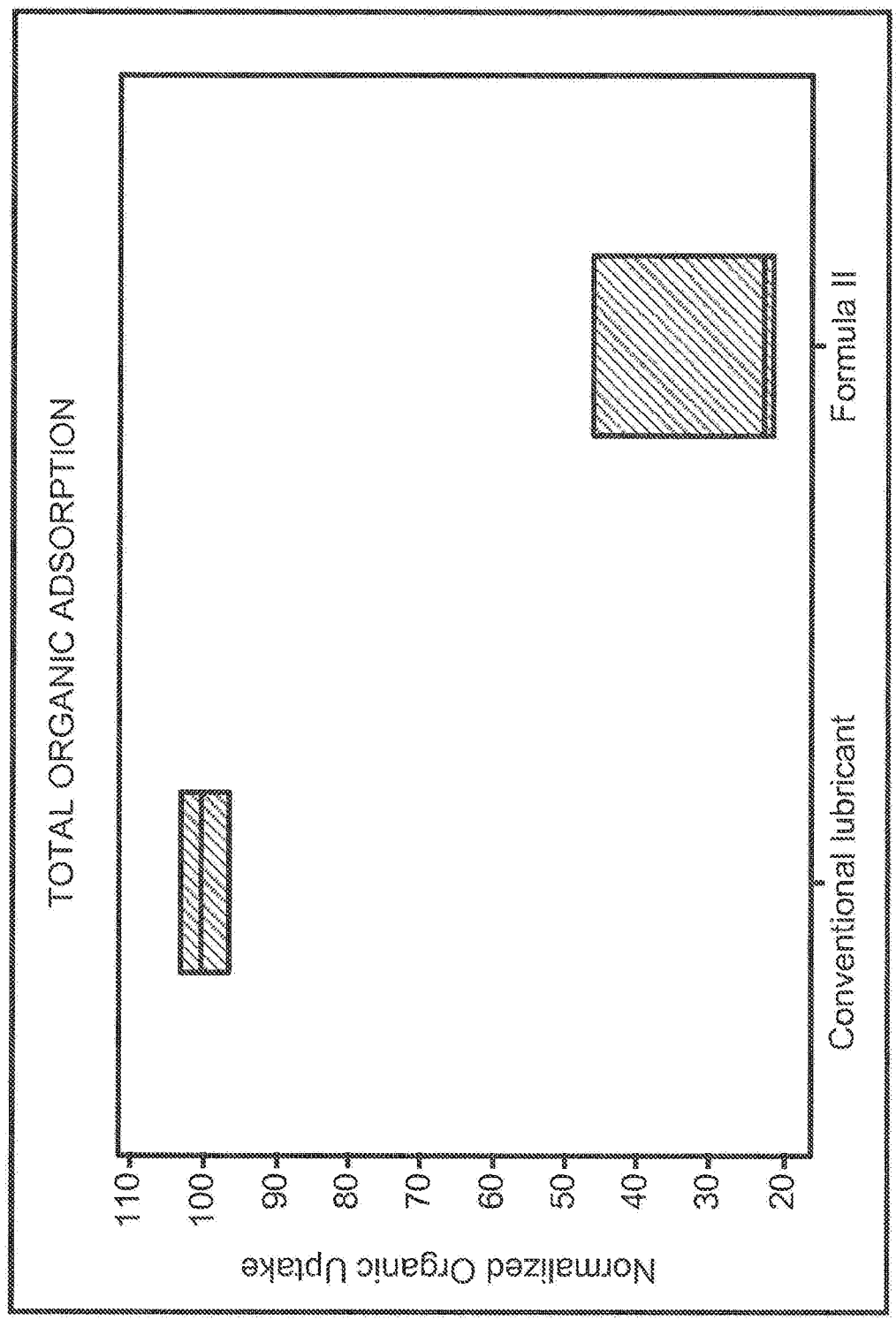
FIG. 6 is a graph comparing putative total organic contamination ("TOC") pick-up for a conventional lubricant and a lubricant including a compound selected from Formulas I and II in accordance with some embodiments.

FIG. 6 is a graph comparing putative TOC pick-up or total organic adsorption for (A) a conventional lubricant (e.g., Z-Tetraol) and (B) a lubricant including a compound selected from Formulas I and II. Organic contaminants such as hydrocarbons may compromise head-storage media interface reliability by adsorption onto the storage media surface and subsequent accumulation onto the read-write head. One function of a lubricant is to provide an inert barrier film to block adsorption of any contaminants that might be present in the disk drive (e.g., due to outgassing from other drive internal components). Data such as that in FIG. 6 may be collected by exposing media coated with different lubricants to model organic contaminants at elevated temperature in a closed system, followed by extraction and quantification of the amount absorbed. Lubricants including one or more compounds such as that of Formula I and/or II may show a significant reduction in the level of adsorbed contamination as compared to the conventional lubricant.

While some particular embodiments have been provided herein, and while the particular embodiments have been provided in some detail, it is not the intention of the applicant(s) for the particular embodiments to limit the scope of the concepts provided herein. Additional adaptations and/or modifications may readily appear to persons having ordinary skill in the art, and, in broader aspects, these adaptations and/or modifications may be encompassed as well. Accordingly, departures may be made from the particular embodiments provided herein without departing from the scope of the concepts provided herein.

What is claimed is:

1. A lubricant composition comprising one or more compounds of Formula I:

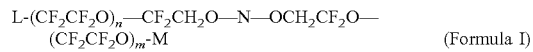
(Formula I)

wherein

L is selected from the group consisting of $R_1CH_2CH_2CH_2$—$OCH_2CF_2O$, $R_1CH_2CHR_1CH_2$—$OCH_2CF_2O$, and $R_1CH_2CHR_1CHR_1$—$OCH_2CF_2O$, M is selected from the group consisting of $CF_2CH_2O$—$CH_2CH_2CH_2R_2$, $CF_2CH_2O$—$CH_2CHR_2CH_2R_2$, and $CF_2CH_2O$—$CHR_2CHR_2CH_2R_2$, and N is $CH_2CHR_3CH_2$;

wherein each instance of $R_1$, $R_2$, and $R_3$ is independently selected from the group consisting of hydroxyl, alkoxyl, carbocycyl, phenyl, heterocycyl, piperonyl, carboxyl, alkylamido, acetamido, carbamoyl, N-alkylcarbamoyl, N,N-dialkylcarbamoyl, 2,3-dihydroxy-1-propoxyl, acryloyl, alkacryloyl, methacryloyl, a substituent of methyl methacrylate, and a substituent of glycidyl ether; and wherein $n \geq 1$, $m \geq 1$, and n and m are the same or different.

2. The lubricant composition of claim 1, wherein L is

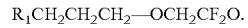

3. The lubricant composition of claim 1, wherein M is $CF_2CH_2O$—$CH_2CH_2CH_2R_2$.

4. The lubricant composition of claim 1, wherein the molecular weight of one or more of the compounds is about 1000 Da to about 7000 Da.

5. The lubricant composition of claim 1, wherein the molecular weight of one or more of the compounds is about 2000 Da to about 4000 Da.

6. The lubricant composition of claim 1, wherein n=1, and wherein m=1.

7. The lubricant composition of claim 1, wherein L is $R_1CH_2CH_2CH_2$—$OCH_2CF_2O$, and wherein R1 is hydroxyl.

8. The lubricant composition of claim 1, wherein M is $CF_2CH_2O$—$CH_2CH_2CH_2R_2$, and wherein R2 is hydroxyl.

9. The lubricant composition of claim 1, wherein $R_3$ is hydroxyl.

10. The lubricant composition of claim 1, wherein the structure of one or more of the compounds is of Formula II

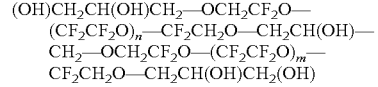

wherein $n \geq 1$, $m \geq 1$, and n and m are the same or different.

11. A method of lubricating a media storage layer surface in an apparatus, the method comprising the step of applying a lubricant composition of claim 1 over a surface to be lubricated.

12. The method of claim 11, wherein the lubricant layer is a thin film having a thickness from about 5 Angstroms to about 50 Angstroms.

13. The method of claim 12, wherein the lubricant layer is a thin film having a thickness from about 8 Angstroms to about 40 Angstroms.

14. The method of claim 13, wherein the lubricant layer is a thin film having a thickness from about 10 Angstroms to about 200 Angstroms.

15. The method of claim 11, wherein the relative touchdown spacing of the lubricant composition of claim 1 on a media storage layer is more than 2 Angstroms compared to the touchdown spacing of Z-Tetraol.

16. The method of claim 11, wherein the total organic adsorption of the lubricant composition of claim 1 on a media storage layer is less than 45 percent of the total organic adsorption of Z-Tetraol.

17. A surface-coated media storage apparatus made by the steps of:
 (a) providing a substrate,
 (b) depositing a thin film onto the substrate to create a seed layer,
 (c) depositing a thin film onto the seed layer to create a magnetic layer,
 (d) depositing a thin film onto the magnetic layer to create a protective layer,
 (e) depositing a lubricant onto the protective layer,
 wherein the lubricant layer comprises the composition of claim 1.

18. The surface-coated media storage apparatus of claim 17, wherein the substrate is selected from nickel-phosphorous-plated aluminum or glass disk.

19. The surface-coated media storage apparatus of claim 17, wherein the seed layer is chromium.

20. The surface-coated media storage apparatus of claim 17, wherein magnetic layer is applied at a thickness of about 500 Angstroms and is a magnetic alloy comprising cobalt, platinum, and/or chromium, and
 the protective layer is diamond-like carbon and is about or less than 150 Angstroms thick.

* * * * *